United States Patent
Yoshizawa et al.

(10) Patent No.: US 7,585,982 B2
(45) Date of Patent: Sep. 8, 2009

(54) METHODS FOR PRODUCING ISOINDOLE DERIVATIVES

(75) Inventors: Kazuhiro Yoshizawa, Kashima-gun (JP); Taiju Nakamura, Kashima-gun (JP); Shigeto Negi, Kashima-gun (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 10 days.

(21) Appl. No.: 11/573,814

(22) PCT Filed: Jul. 27, 2005

(86) PCT No.: PCT/JP2005/013696

§ 371 (c)(1),
(2), (4) Date: Sep. 25, 2007

(87) PCT Pub. No.: WO2006/018955

PCT Pub. Date: Feb. 23, 2006

(65) Prior Publication Data

US 2008/0214834 A1 Sep. 4, 2008

(30) Foreign Application Priority Data

Aug. 16, 2004 (JP) .............................. 2004-236645

(51) Int. Cl.
*C07D 209/44* (2006.01)
(52) U.S. Cl. ...................... 548/471; 558/422
(58) Field of Classification Search ................. 548/471; 558/422
See application file for complete search history.

(56) References Cited

U.S. PATENT DOCUMENTS

| 2005/0004204 A1 | 1/2005 | Suzuki et al. |
| 2006/0058370 A1 | 3/2006 | Shimomura et al. |
| 2008/0045753 A1 | 2/2008 | Yoshikawa |

FOREIGN PATENT DOCUMENTS

JP    CA2446924    * 10/2003

WO    WO 02/085855 A1 * 10/2002
WO    WO 2004/078721 A1    9/2004

OTHER PUBLICATIONS

Walter Hartung J. Am. Chem. Soc., 1928, 50 (12), 3370-3374.*
Wolff, Manfred E. Burger's Medicinal Chemistry, 4ed, Part I, John Wiley & Sons, 1980, pp. 336-337.*

* cited by examiner

*Primary Examiner*—Valerie Rodriguez-Garcia
(74) *Attorney, Agent, or Firm*—Townsend and Townsend and Crew LLP

(57) ABSTRACT

The present invention relates to a method for producing an isoindole derivative (compound (II)) with the following general formula (II):

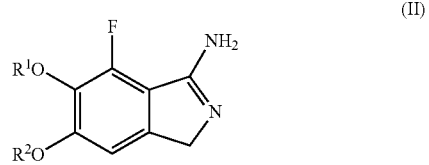

(II)

(wherein $R^1$ and $R^2$ each independently represents a $C_{1-6}$ alkyl group) or a salt thereof, comprising the step of cyclizing, in a solvent, compound (I) with the following general formula (I):

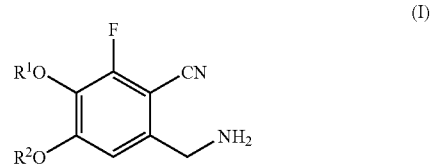

(I)

(wherein $R^1$ and $R^2$ have the same meanings as $R^1$ and $R^2$ in formula (II) above) or a salt thereof, or their hydrate or solvate in the presence of a base (Step 1).

6 Claims, No Drawings

METHODS FOR PRODUCING ISOINDOLE DERIVATIVES

This application is a U.S. National Phase of PCT/JP2005/013696, filed Jul. 27, 2005, which claims priority to Japanese Patent Application No. 2004-236645, filed Aug. 16, 2004. The contents of all of the aforementioned applications are hereby incorporated by reference in their entirety.

TECHNICAL FIELD

The present invention relates to methods for producing isoindole derivatives.

BACKGROUND ART

One example of an antithrombosis approach is a method that inhibits the enzyme activity of thrombin. Compounds having an antagonistic effect on thrombin receptors are recently anticipated to exert a prominent effect in the treatment and prevention of diseases in which thrombin is involved, for example, thrombosis, vascular restenosis, deep venous thrombosis, pulmonary embolism, cerebral infarction, heart diseases, disseminated intravascular coagulation syndrome, hypertension, inflammatory diseases, rheumatism, asthma, glomerulonephritis, osteoporosis, neurological disorders, and malignant tumors. Therefore, thrombin receptor antagonists that satisfy points such as pharmacological activity, specificity for thrombin receptors, safety, dose, and oral effectiveness were needed.

2-Iminopyrrolidine derivatives and salts thereof have already been found to have a prominent inhibitory activity on thrombin receptors and to be useful as thrombin receptor antagonists (Patent Document 1: WO 02/085855). Among the 2-iminopyrrolidine derivatives and salts thereof, Patent Document 1 describes methods for producing, for example, compounds having the following formula (A1):

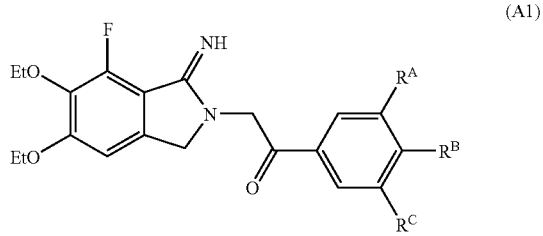

(wherein $R^A$ represents a $C_{1-6}$ alkyl group, $R^B$ represents a $C_{1-6}$ alkoxy group, and $R^C$ represents a 5-14 membered heterocyclic group), or salts thereof.

Furthermore, Patent Document 1 above describes that an isoindole-containing derivative (A2) having the following formula may be an important intermediate in the production of the aforementioned A1 compounds, and describes a method for producing the isoindole derivative (A2), wherein 4,5-diethoxy-3-fluorophthalonitrile (A3) as shown below is dissolved in ethyl acetate-ethanol-methanol and reacted after addition of platinum oxide (Step 4 and such in Example 7 of Patent Document 1). (Unless otherwise specified, "Et" represents an ethyl group in the present description.)

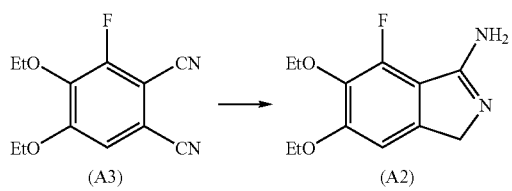

[Patent Document 1] WO 02/085855.

DISCLOSURE OF THE INVENTION

Problems to be Solved by the Invention

However, with the method described above, the yield of the compound of interest is low, many byproducts are produced, and the products must be purified immediately after the reaction because of their poor stability. Furthermore, since the products are highly adsorptive to platinum catalysts, treatment is required to avoid the risk of fire caused by the platinum catalyst remained even after filtration, thus the method is problematic in that the purification is complicated. In addition, since platinum catalysts are expensive, there is a problem of cost when they are heavily used at an industrial scale.

Therefore, methods for producing the aforementioned isoindole derivatives, or salts thereof, that are low cost and have easy and safe reaction procedures and purification methods, high regioselectivity of reduction, and good yield are anticipated. Thus, an objective of the present invention is to provide isoindole derivative-producing methods that are also useful for industrial scale production.

Means to Solve the Problems

The present inventors conducted dedicated research to solve the above-mentioned problems. They completed the present invention by discovering that the novel intermediate compounds (I) below, in which the cyano group in the meta position to fluorine has been reduced regioselectively, can be obtained by hydrogenating, in a solvent, compounds (III) with the following formula (III) in the presence of a palladium catalyst and an acid, and that as a result, isoindole derivatives (II) that have been cyclized in the presence of a base can be obtained in high yield.

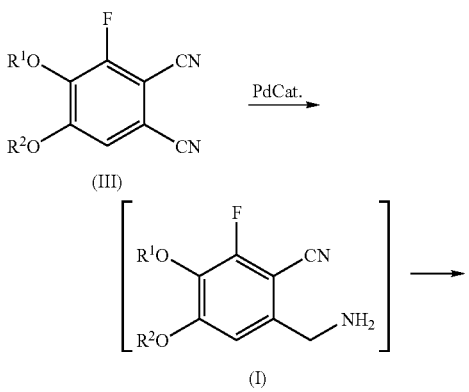

-continued

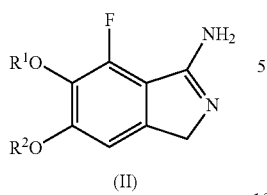

(II)

Therefore, the present invention comprises the following:

[1] a method for producing an isoindole derivative (compound (II)) with the following general formula (II):

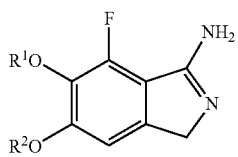

(II)

(wherein $R^1$ and $R^2$ each independently represents a $C_{1-6}$ alkyl group) or a salt thereof, comprising the step of cyclizing, in a solvent, compound (I) with the following general formula (I):

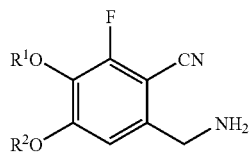

(I)

(wherein $R^1$ and $R^2$ have the same meanings as $R^1$ and $R^2$ in formula (II) above) or a salt thereof, or their hydrate or solvate in the presence of a base (Step 1);

[2] the method of [1], further comprising the step of hydrogenating, in a solvent, compound (III) with the following general formula (III):

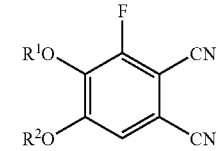

(III)

(wherein $R^1$ and $R^2$ have the same meanings as $R^1$ and $R^2$ in formula (I) above in [1]) in the presence of a palladium catalyst and an acid to obtain compound (I) having the following general formula (I):

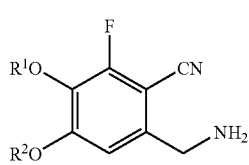

(I)

(wherein $R^1$ and $R^2$ have the same meanings as $R^1$ and $R^2$ in formula (I) above) (Step 2);

[3] the method of [2], wherein the palladium catalyst is palladium hydroxide, a palladium-carbon catalyst, or Lindlar catalyst;

[4] the method of [2] or [3], wherein the acid is methanesulfonic acid or sulfuric acid;

[5] the method of any one of [1] to [4], wherein $R^1$ and $R^2$ in formulae (I) to (III) are both ethyl groups;

[6] a compound with the following general formula (I):

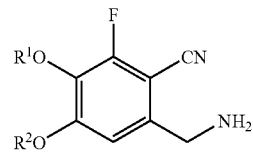

(I)

(wherein $R^1$ and $R^2$ each independently represents a $C_{1-6}$ alkyl group) or a salt thereof, or their hydrate or solvate; and

[7] the compound of [6] or a salt thereof or their hydrate or solvate, wherein $R^1$ and $R^2$ in the formula (I) above are both ethyl groups.

The isoindole derivatives described above have tautomers represented by formula (II-1) below. In the present description, the isoindole derivatives represented by formula (II) comprise tautomers having represented by formula (II-1):

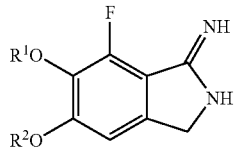

(II-1)

(wherein $R^1$ and $R^2$ each have the same meaning as $R^1$ and $R^2$ in the formula (I) above).

EFFECTS OF THE INVENTION

According to the present invention, the cyano group in the 1st position (meta position to fluorine) of 4,5-dialkoxy-3-fluorophthalonitrile (compounds (III)) can be reduced with significantly high regioselectivity by hydrogenating, in a solvent, compounds (III) in the presence of a palladium catalyst and an acid to produce 6-aminomethyl-3,4-dialkoxy-2-fluorobenzonitrile (compounds (I)) which can be further cyclized in the presence of a base and purified to obtain a good yield of 5,6-dialkyloxy-7-fluoro-3H-isoindol-1-ylamine (compounds (II)).

Also, according to the present invention, purification and isolation of the compounds of interest can be performed very easily, since the palladium catalyst used is inexpensive and safe with low fire risk, and purification can be carried out by only filtration, extraction, and crystallization, without the need for complicated procedures such as chromatography. Therefore, the methods of the present invention are significantly advantageous for producing isoindole derivatives at an industrial scale compared to conventional technologies.

BEST MODE FOR CARRYING OUT THE INVENTION

Step 1

The method of the present invention for producing isoindole derivatives or salts thereof comprises Step 1 in which compounds (I) or salts thereof, or their hydrates or solvates, are cyclized in the presence of a base to obtain compounds (II) or salts thereof. Moreover, the compounds (I) produced in Step 2 described below may be cyclized in the presence of a base according to Step 1 after Step 2.

Namely, compounds (I) or salts thereof, or their hydrates or solvates, or isoindole derivatives (II) which are cyclized compounds (I), or salts thereof, can be obtained by cyclizing in the presence of a base, compounds (I) that are produced by regioselective reduction according to Step 2 described below, followed by extraction or crystallization.

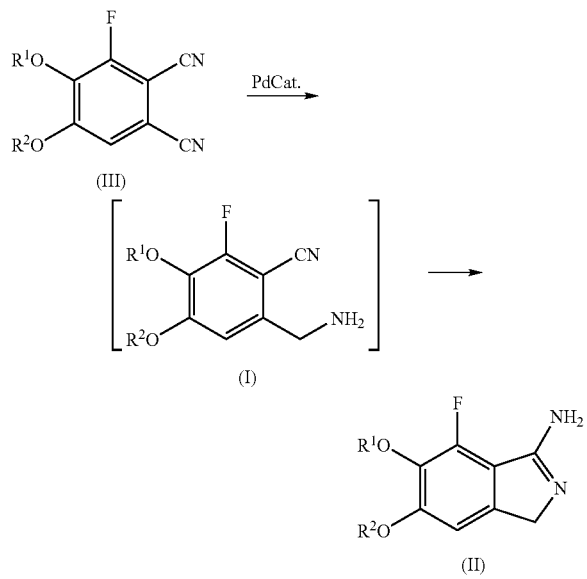

In the above formula, $R^1$ and $R^2$ each independently represent a $C_{1-6}$ alkyl group.

The term "$C_{1-6}$ alkyl group" refers to a linear or branched alkyl group of one to six carbons, which is a monovalent group induced by removing any one of the hydrogen atoms from an aliphatic hydrocarbon of one to six carbons.

Specifically, the $C_{1-6}$ alkyl group includes, for example, methyl, ethyl, 1-propyl, 2-propyl, 2-methyl-1-propyl, 2-methyl-2-propyl, 1-butyl, 2-butyl, 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,3-dimethyl-1-butyl, 3,3-dimethyl-1-butyl, 2,2-dimethyl-1-butyl, 2-ethyl-1-butyl, 3,3-dimethyl-2-butyl, and 2,3-dimethyl-2-butyl groups.

Among these groups, a methyl group or an ethyl group is preferable, and an ethyl group is further preferable.

The salts of compounds (I) described above include salts with inorganic acids such as sulfuric acid, hydrochloric acid, and nitric acid; and salts with sulfonic acids such as sulfonic acid, methanesulfonic acid, ethanesulfonic acid, benzenesulfonic acid, and toluenesulfonic acid.

When placed in the atmosphere, compounds (I) described above may absorb moisture or water and become hydrates, and such hydrates can also be used in the present invention. In addition, compounds (I) may absorb some other solvents and become solvates, and such solvates may also be used in the present invention.

For the base, sodium hydroxide, potassium hydroxide, triethylamine, ammonia, diisopropylethylamine, diisopropylamine, sodium hydrogen carbonate, sodium carbonate, sodium acetate, or the like can be used.

The base is preferably used in an amount of 0.1 to 5 equivalents, and more preferably 0.1 to 2 equivalents of compounds (I).

The reaction temperature depends on conditions such as the catalyst used and the boiling point of the solvent, but is preferably −25° C. to 100° C. When a strong base such as sodium hydroxide is used, the reaction temperature is more preferably 10° C. to 30° C. When a weak base such as triethylamine is used, the reaction temperature is more preferably 40° C. to 80° C.

The reaction duration is usually one to 100 hours.

The obtained isoindole derivatives (II) can be easily isolated/purified by extraction and crystallization. For example, the isoindole derivatives (II) are crystallized and can be isolated/purified, by extracting isoindole derivatives (II) into the aqueous layer under acidic condition, adjusting the pH of the aqueous solution, washing away impurities with an organic solvent, and basifying the washed aqueous solution.

The pH of the above aqueous solution during washing is preferably not more than 8.5, and more preferably 7.5 to 8.5.

As an organic solvent for washing the aqueous solution, ethyl acetate, isopropyl acetate, methyl-t-butyl ether (MTBE), diethyl ether, toluene, xylene, heptane, hexane, or the like can be used. These solvents can be used alone or in a combination of two types or more.

The pH of the aqueous solution during crystallization is preferably not less than 10.5.

The isoindole derivatives (II) produced can be crystallized and isolated in the form of salts such as sulfates, by adding an acid into the reaction system. The isoindole derivatives (II), which are strongly basic amines, may undergo degradation such as coloration, and can be made into acid salts such as sulfates for stabilization and long-term storage of compounds.

For example, the isoindole derivatives (II) can be crystallized and isolated/purified as salts by concentrating a reaction solution comprising the isoindole derivatives (II), dissolving the residue in a solvent, and further adding an acid thereto. Moreover, even when the solvent is not distilled off from the reaction solution, the isoindole derivatives (II) can be crystallized and isolated/purified as salts by adding a solvent or an acid.

There is no particular limitation on the salt-forming acid, as long as it forms salts with isoindole derivatives (II) and is pharmaceutically acceptable.

The solvents used for forming salts include DME, THF, MTBE, ethyl acetate, isopropyl acetate, toluene, xylene, heptane, hexane, methanol, ethanol, 1-propanol, 2-propanol, and water, and these solvents can be used alone or in a combination of two types or more.

The benzylamine derivatives (I) obtained in Step 2 described below can also be crystallized and isolated/purified in the form of salts by adding an acid after base addition.

For example, benzylamine derivatives (I) can be crystallized and isolated/purified as salts, by distilling off the solvent of a reaction solution comprising the benzylamine derivatives (I) obtained in Step 2, dissolving the residue in a solvent, adding a base thereto, and adding an acid immediately afterward. Moreover, even when the solvent is not distilled off from the reaction solution, benzylamine derivatives (I) can be crystallized and isolated/purified as salts by adding a solvent or an acid.

The temperature for distilling off the solvent is preferably not higher than 30° C.

The solvents used for dissolving residues or forming salts include DME, THF, MTBE, ethyl acetate, isopropyl acetate, toluene, xylene, heptane, hexane, methanol, ethanol, 1-propanol, 2-propanol, and water, and these solvents can be used alone or in a combination of two types or more.

Preferably, the solvent is DME or MTBE.

The temperature for adding the base is preferably not higher than 10° C.

There is no particular limitation on the salt-forming acid, as long as it forms salts with benzylamine derivatives (I) and is pharmaceutically acceptable.

Salts of benzylamine derivatives (I) can also be obtained without adding an acid after base treatment.

For example, crystals of sulfate ½ triethylamine solvates of benzylamine derivatives (I) can be isolated/purified by carrying out a hydrogenation reaction using sulfuric acid as an acid in Step 1, distilling off the solvent, dissolving in a solvent the residue comprising benzylamine derivatives (I), and adding triethylamine thereto.

The solvents used for dissolving residues or forming salts include DME, methanol, ethanol, 1-propanol, and 2-propanol, and these solvents can be used alone or in a combination of two types or more.

Furthermore, cyclization of the salts of benzylamine derivatives (I) to form isoindole derivatives (II) can be achieved quantitatively by treatment with a strong base such as sodium hydroxide or treatment with a weak base such as triethylamine at an elevated temperature as described above.

Step 2

The method of the present invention for producing the isoindole derivatives may comprise the step of hydrogenating, in a solvent, compounds (III) of the general formula (III) below:

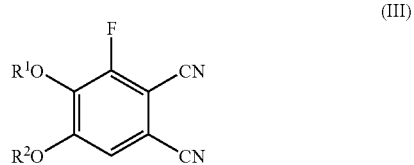

(III)

in the presence of a palladium catalyst and an acid (Step 2).

In the formula above, $R^1$ and $R^2$ have the same meaning as above.

The palladium catalyst described above includes palladium compounds such as palladium, palladium hydroxide, and palladium oxide. The catalyst is preferably a palladium compound supported on a carrier. Lindlar catalyst and such can also be used preferably.

The carrier for the aforementioned supported palladium compound is preferably carbon, silica-alumina, alumina, silica, calcium carbonate, barium carbonate, or barium sulfate, more preferably carbon, alumina, or barium sulfate, and particularly preferably carbon.

In the supported palladium compound described above, the amount of active ingredient supported in relation to the carrier is preferably 0.5 to 30% by weight, more preferably 1 to 30% by weight, and still more preferably 5 to 25% by weight.

Of these, a palladium hydroxide catalyst supported on carbon ($Pd(OH)_2/C$), a palladium carbon catalyst (Pd/C), or Lindlar catalyst is preferable, and $Pd(OH)_2/C$ or Pd/C is more preferable.

The palladium catalyst described above may be a hydrate, and the water content is preferably 10 to 70% by weight relative to the total amount of the palladium compound and water.

The amount of palladium catalyst used may be the so-called catalytic amount, and is preferably 1 to 50% relative to the substrate compound by weight, and more preferably 5 to 30% by weight, without specific limitations.

The reaction solvent is preferably one that does not undergo hydrogenation reaction, and more preferably one that is dissolved in acids.

Specifically, the solvent includes 1,2-dimethoxyethane (DME), 1,4-dioxane, tetrahydrofuran (THF), methanol, ethanol, 1-propanol, 2-propanol, and water, and of these, DME is preferable. These solvents can be used alone or in a combination of two types or more.

The acid for the hydrogenation reaction described above preferably includes methanesulfonic acid, ethanesulfonic acid, toluenesulfonic acid, benzenesulfonic acid, sulfuric acid, acetic acid, and trifluoroacetic acid, and more preferably is methanesulfonic acid or sulfuric acid.

In particular, when the aforementioned Lindlar catalyst is used, sulfuric acid is preferably used as the acid. When $Pd(OH)_2/C$ or Pd/C described above is used, preferably methanesulfonic acid or sulfuric acid, and more preferably methanesulfonic acid is used as the acid.

The amount of acid added is preferably not less than 0.5 equivalents, more preferably not less than one equivalent, and still more preferably one to three equivalents of the substrate compound.

The presence of such an acid can improve the rate of regioselective hydrogenation reaction.

The hydrogen pressure in the hydrogenation reaction is preferably 0.1 to 10 MPa, and more preferably 0.3 to 2 MPa.

The reaction temperature depends on the conditions of the catalyst used and the boiling point of the solvent, but is preferably −25 to 30° C., and more preferably −15 to 10° C. The reaction duration is usually one to 100 hours.

After completion of the hydrogenation reaction, products can be obtained by filtering off the palladium catalyst and washing.

The washing solvent preferably includes methanol, ethanol, 1-propanol, 2-propanol, and water, and is more preferably methanol or water. These solvents can be used alone or in a combination of two types or more.

The compounds of the present invention are compounds with the following general formula (I):

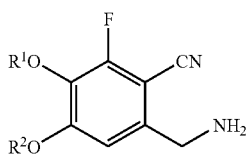

or salts thereof or their hydrates. The compounds with the general formula (I) above are novel compounds.

In the above formula, $R^1$ and $R^2$ each independently represent a $C_{1-6}$ alkyl group. As $C_{1-6}$ alkyl group, $R^1$ and $R^2$ are preferably both a $C_{1-6}$ alkyl group, more preferably both a $C_{1-3}$ alkyl group, more preferably both a methyl or ethyl group, and particularly preferably both an ethyl group.

These compounds are useful as intermediates when producing 2-iminopyrrolidine derivatives that are useful as thrombin receptor antagonists (Patent Document 1), for example, compounds having the following formula (A1):

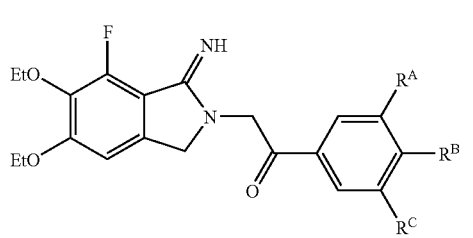

or salts thereof. In the above formula, $R^A$ represents a $C_{1-6}$ alkyl group, $R^B$ represents a $C_{1-6}$ alkoxy group, and $R^C$ represents a 5-14 membered heterocyclic group.

All prior art references cited herein are incorporated by reference into this description.

EXAMPLES

Herein below, the present invention will be specifically described with reference to Examples, but it is not to be construed as being limited thereto. In the present description, room temperature refers to a temperature within the range of 20° C. to 30° C., and preferably refers to a temperature of about 25° C.

Preparation Example 1

Production of 4,5-diethoxy-3-fluorophthalonitrile

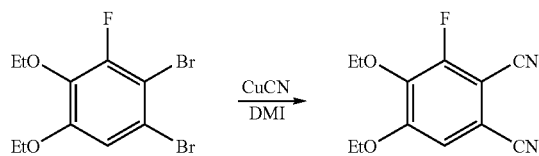

A mixture of 1,2-dibromo-4,5-diethoxy-3-fluorobenzene (137.0 g, 0.401 mol, content: 81%), copper cyanide (107.5 g, 1.200 mol) and 1,3-dimethyl-2-imidazolidinone (600 mL) was subjected to nitrogen substitution under reduced pressure, then heated and stirred at 130° C. for 17 hours and at 140° C. for four hours under nitrogen atmosphere.

After the reaction mixture was cooled to room temperature, N,N-dimethylformamide (600 mL), toluene (1.2 L) and concentrated aqueous ammonia (1.2 L) were added thereto, and the layers were separated. The resultant organic layer was washed by adding N, N-dimethylformamide (411 mL) and concentrated aqueous ammonia (800 mL). The organic layer was further washed sequentially with a 25% aqueous solution of ethylenediamine (1.2 L), 1N hydrochloric acid (1.2 L), and water (1.2 L), filtered through activated carbon, and concentrated at 50° C. under reduced pressure to give a yellow sherbet-like residue. The residue was dissolved by adding toluene (100 mL) and no-heptane (100 mL) and heating to 60° C., and the solution was cooled to 10° C. or lower by stirring, to precipitate crystals which were then filtered. The resultant crystals were dissolved by adding toluene (50 mL) and no-heptane (50 mL) and heating to 90° C., and the solution was stirred at room temperature to precipitate crystals. After cooling to 10° C. or lower, the crystals were filtered, and dried at 50° C. under reduced pressure to give 51.5 g of the title compound (yield: 55%) as white crystals.

Example 1

Production of 5,6-diethoxy-7-fluoro-3H-isoindol-1-ylamine

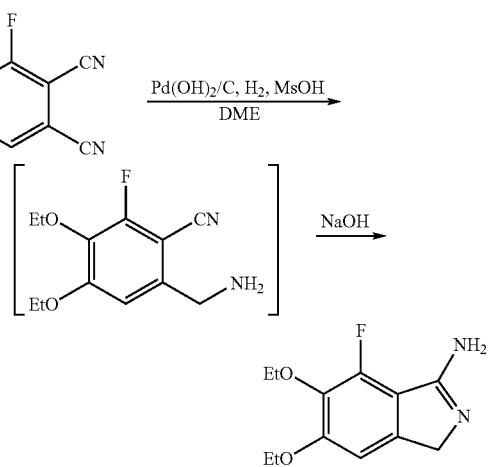

A mixture of 4,5-diethoxy-3-fluorophthalonitrile (100 g, 0.427 mol) produced in Preparation Example 1, methanesulfonic acid (36 mL, 0.555 mol), 20% palladium hydroxide-carbon (12.5 g, 50% hydrate) (20% palladium hydroxide-carbon catalyst (wet), Awaken Fine Chemicals Co., Ltd.) and 1,2-dimethoxyethane (500 mL) was stirred at 7° C. under hydrogen atmosphere (1 MPa) for 27 hours. After water (1 L) was added to the reaction mixture, insoluble matter was filtered off, and the residue was washed with water (500 mL).

The filtrates were combined, a 5N aqueous solution of sodium hydroxide was added until the pH reached 5.4, and the solution was stirred at room temperature for 18 hours. After toluene (500 mL) and ethyl acetate (100 mL) were added thereto, 5N hydrochloric acid was added until the pH of the aqueous layer reached 3.7, and the layers were separated. After ethyl acetate (500 mL) was added to the resultant aqueous layer, a 5N aqueous solution of sodium hydroxide was added until the pH of the aqueous layer reached 8.0, and the layers were separated. The resultant aqueous layer was washed sequentially with ethyl acetate (500 mL), toluene (500 mL), and toluene (500 mL). A 5N aqueous solution of sodium hydroxide was added to the aqueous layer on ice until the pH reached 12.0, and the precipitated crystals were filtered and dried at 40° C. under reduced pressure to give 82.7 g of the title compound (yield: 82%) as slightly yellowish white crystals.

Example 2

Production of 5,6-diethoxy-7-fluoro-3H-isoindol-1-ylamine sulfate

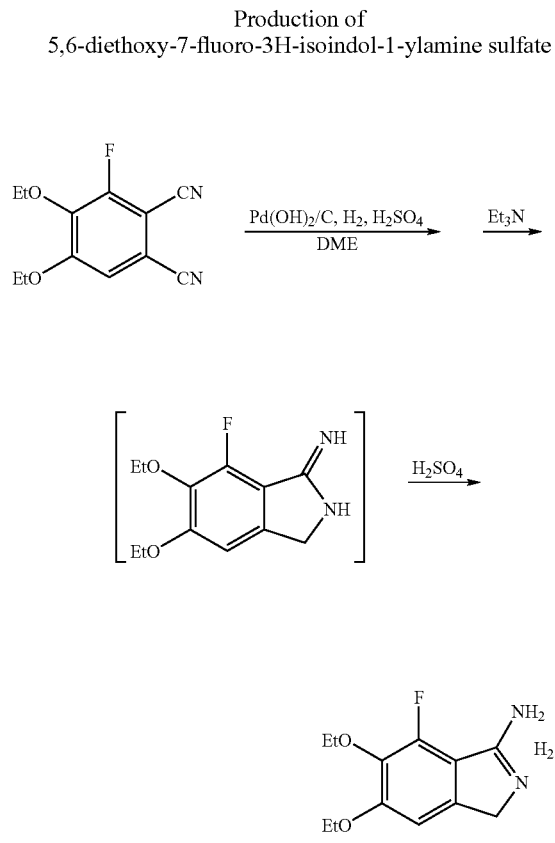

A mixture of 4,5-diethoxy-3-fluorophthalonitrile (2.34 g, 10 mol) prepared in Preparation Example 1, sulfuric acid (0.56 mL, 10 mol), 20% palladium hydroxide-carbon (0.59 g, 50% hydrate) (20% palladium-carbon powder, palladium hydroxide type (hydrate), N.E. Chemical Corporation) and 1,2-dimethoxyethane (23 mL) was stirred at −23° C. under hydrogen atmosphere (atmospheric pressure) for 29 hours. After insoluble matter in the reaction mixture was filtered off, the residue was washed with methanol (23 mL), and the combined filtrate was divided into five equal portions. To one of them, triethylamine (0.14 mL, 1 mol) was added, and the mixture was stirred at 60° C. for three hours and concentrated at 40° C. under reduced pressure. Methanol (2.3 mL) and 1,2-dimethoxyethane (6.9 mL) were added to the residue, then sulfuric acid (0.11 mL, 2 mol) was added on ice, and the mixture was stirred. Precipitated crystals were filtered, washed with a 5% methanol-1,2-dimethoxyethane solution, and dried at room temperature under reduced pressure to give 0.45 g of the title compound (yield: 72%) as grayish white crystals.

$^1$H-NMR (400 MHz, DMSO-d6) δ: 1.28 (3H, t, J=7.1 Hz), 1.39 (3H, t, J=7.1 Hz), 4.08 (2H, q, J=7.1 Hz), 4.19 (2H, q, J=7.1 Hz), 4.72 (2H, so), 7.27 (1H, so), 8.80 (1H, bus), 9.27 (1H, bus), 9.77 (1H, bush), 10.04 (1H, bus).

Example 3

Production of 5,6-diethoxy-7-fluoro-3H-isoindol-1-ylamine

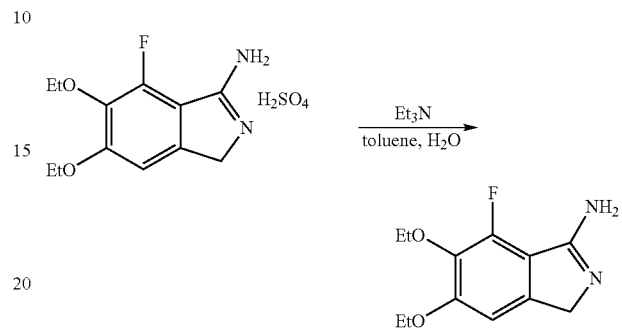

Triethylamine (0.13 mL) was added to a mixture of 5,6-diethoxy-7-fluoro-2,3-dihydroisoindol-1-ylideneamine sulfate (225 mg, 0.67 mol) produced in Example 2, water (2.3 mL) and toluene (2.3 mL). The mixture was stirred at room temperature. After the layers were separated, the organic layer was re-extracted with water (1.2 mL), the aqueous layers were combined, and a 5N aqueous solution of sodium hydroxide (0.3 mL) was added thereto on ice. The mixture was stirred on ice, and then precipitated crystals were filtered and dried at room temperature under reduced pressure to give 133 mg of the title compound (yield: 84%) as grayish white crystals.

Example 4

Production of 6-aminomethyl-3,4-diethoxy-2-fluorobenzonitrile sulfate

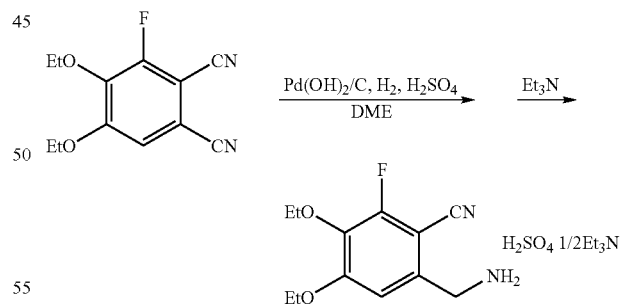

A mixture of 4,5-diethoxy-3-fluorophthalonitrile (2.34 g, 10 mol) prepared in Preparation Example 1, sulfuric acid (0.56 mL, 10 mol), 20% palladium hydroxide-carbon (0.59 g, 50% hydrate) (20% palladium-carbon powder, palladium hydroxide type (hydrate), N.E. Chemical Corporation) and 1,2-dimethoxyethane (23 mL) was stirred at −22° C. under hydrogen atmosphere (atmospheric pressure) for 24 hours. After insoluble matter in the reaction mixture was filtered off, the residue was washed with methanol (23 mL) and the combined filtrate was divided into five equal portions. After one of them was concentrated at room temperature under reduced pressure, 1,2-dimethoxyethane (9.2 mL) was added thereto, and the mixture was stirred. Then, triethylamine (0.56 mL, 4 mol) was added dropwise thereto and the mixture was stirred at room temperature for one hour. Precipitated crystals were filtered, washed with a 5% methanol-1,2-dimethoxyethane solution, and dried at room temperature under reduced pressure to give 0.59 g of the ½ triethylamine solvate of the title compound (yield: 76%) as dark white crystals.

$^1$H-NMR (400 MHz, DMSO-d6) δ: 1.11 (9/2H, t, J=7.1 Hz), 1.24 (3H, t, J=7.1 Hz), 1.38 (3H, t, J=7.1 Hz), 2.93 (6/2H, q, J=7.1 Hz), 3.90 (2H, so), 4.06 (2H, q, J=7.1 Hz), 4.19 (2H, q, J=7.1 Hz), 7.25 (1H, so).

Example 5

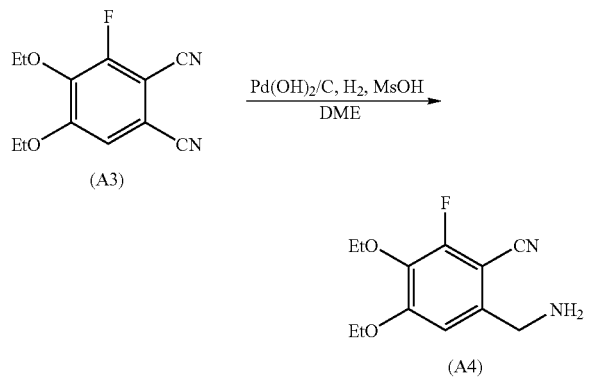

A mixture of 20% palladium hydroxide-carbon (50% hydrate) (20% palladium-carbon powder, palladium hydroxide type (hydrate), N.E. Chemical Corporation), methanesulfonic acid and 1,2-dimethoxyethane (DME) at ratios (as shown in Table 1) relative to the 4,5-diethoxy-3-fluorophthalonitrile (compound A3) produced in Preparation Example 1 was stirred under hydrogen atmosphere. The hydrogen pressure, reaction temperature, and reaction time are each shown in Table 1. After water was added to the reaction mixture, insoluble matter was filtered off from the reaction mixture, and the residue was washed with water. The resultant reaction mixture was analyzed by HPLC, and the yield of the reaction product (compound A4) was calculated.

HPLC was performed under the following conditions:

Column: Chemicals Inspection and Testing Institute, L-Column ODS Waters (4.6×250 mm)

Column temperature: 35° C. Mobile phase: (A) CH$_3$CN/H$_2$O/70% HClO$_4$=300 mL:700 mL: 1 mL (B) CH$_3$CN/H$_2$O/70% HClO$_4$=900 mL:100 mL: 1 mL Gradient Program: time (min)/B conc. (%)=0/0, 8/0, 30/100, 30.01/0, 35/stop Flow rate: 1 mL/min Detection: UV 252 nm RT: 27.2 min (compound A3), 10.0 min (compound A4), 8.5 min (compound A2)

A3: 4,5-diethoxy-3-fluorophthalonitrile

A4: 6-aminomethyl-3,4-diethoxy-2-fluorobenzonitrile sulfate

A2: 5,6-diethoxy-7-fluoro-3H-isoindol-1-ylamine

The results are shown in Table 1.

Examples 6 to 10

Similarly as in Example 5, reactions were performed with the reaction temperatures, hydrogen pressures and reaction time shown in Table 1, using the catalysts, acids and solvents shown in Table 1. The yield of reaction products was calculated in the same way as in Example 5. The results are shown in Table 1.

Comparative Examples 1 to 7

Similarly as in Example 5, reactions were performed with the reaction temperatures, hydrogen pressures and reaction time shown in Table 1, using the catalysts, acids and solvents shown in Table 1. The yield of reaction products was calculated in the same way as in Example 5.

Comparative Example 7 was conducted according to the method described in WO 02/085855. HPLC yield was 65%, but the yield of chromatographic isolation was as low as 20%, because the product was highly adsorptive to platinum catalysts.

The results are shown in Table 1. For Comparative Example 7, the yield of the following compound A2 is shown.

TABLE 1

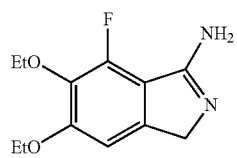

(A2)

| | CATALYST (% BY WEIGHT) | ACID (eq.) | SOLVENT (TIMES VOLUME) | HYDROGEN (MPa) | TEMPERATURE (° C.) | TIME (hr) | YIELD (A4: %) |
|---|---|---|---|---|---|---|---|
| EXAMPLE 5 | Pd(OH)$_2$/C(*1) (10) | MsOH (1.3) | DME (10) | 1.0 | 7 | 21 | 86 |
| EXAMPLE 6 | Pd(OH)$_2$/C(*1) (10) | SULFURIC ACID (1.0) | DME (10) | 1.0 | 7 | 20 | 63 |
| EXAMPLE 7 | Pd/C(*2) (10) | MsOH (1.3) | DME (10) | 1.0 | 7 | 21 | 84 |

TABLE 1-continued (A2)

| | CATALYST (% BY WEIGHT) | ACID (eq.) | SOLVENT (TIMES VOLUME) | HYDROGEN (MPa) | TEMPERATURE (° C.) | TIME (hr) | YIELD (A4: %) |
|---|---|---|---|---|---|---|---|
| EXAMPLE 8 | LINDLAR CATALYST (*3) (25) | SULFURIC ACID (2.0) | DME (10) | 0.5 | 25 | 20 | 60 |
| EXAMPLE 9 | Pd/Al$_2$O$_3$(*4) (10) | MsOH (1.3) | DME (10) | 1.0 | 7 | 21 | 48 |
| EXAMPLE 10 | Pd/BaSO$_4$(*5) (10) | MsOH (1.3) | DME (10) | 1.0 | 7 | 20 | 53 |
| COMPARATIVE EXAMPLE 1 | Rh/C(*6) (10) | MsOH (1.3) | DME (10) | 1.0 | 7 | 20 | 3 |
| COMPARATIVE EXAMPLE 2 | Ru/C(*7) (10) | MsOH (1.3) | DME (10) | 1.0 | 7 | 20 | 0 |
| COMPARATIVE EXAMPLE 3 | Pt/C(*8) (10) | MsOH (1.3) | DME (10) | 1.0 | 7 | 21 | 0 |
| COMPARATIVE EXAMPLE 4 | RANEY Ni(*9) (10) | CONCENTRATED AQUEOUS NH$_3$ (1.3) | DME (10) | 1.0 | 25 | 20 | 0 |
| COMPARATIVE EXAMPLE 5 | RANEY Co(*10) (10) | CONCENTRATED AQUEOUS NH$_3$ (1.3) | DME (10) | 1.0 | 25 | 20 | 0 |
| COMPARATIVE EXAMPLE 6 | PtO$_2$(*11) (10) | MsOH (1.3) | DME (10) | 1.0 | 7 | 21 | 18 |
| COMPARATIVE EXAMPLE 7 | PtO$_2$(*11) (8) | NONE | *12 | ATMOSPHERIC PRESSURE | 25 | 86 | 65 (A2) |

MsOH: methanesulfonic acid, DME: 1,2-dimethoxyethane
*1: 20% Pd(OH)2/C, 50% wet (20% palladium-carbon powder, palladium hydroxide type (hydrate), N.E. Chemcat Corporation)
*2: 5% Pd/C, 50% wet (5% palladium-carbon powder (hydrate), STD type, N.E. Chemcat Corporation)
*3: Lindlar catalyst (Lindlar catalyst, N.E. Chemcat Corporation)
*4: 5% Pd/Al$_2$O$_3$, dry (5% palladium-Alumina powder, N.E. Chemcat Corporation)
*5: 5% Pd/BaSO$_4$, dry (5% palladium-Barium sulfate powder, N.E. Chemcat Corporation)
*6: 5% Rh/C, 50% wet (5% rhodium-carbon powder (hydrate), N.E. Chemcat Corporation)
*7: 5% Ru/C, 50% wet (5% ruthenium-carbon powder (hydrate), B type, N.E. Chemcat Corporation)
*8: 5% Pt/C, 50% wet (5% platinum-carbon powder (hydrate), PE type, N.E. Chemcat Corporation)
*9: Raney Ni (activated nickel catalyst NDHT-90, Kawaken Fine Chemicals Co., Ltd.)
*10: Raney Co (activated cobalt catalyst ODHT-60, Kawaken Fine Chemicals Co., Ltd.)
*11: PtO2 (platinum oxide, Aldrich, Inc.)
*12: ethanol/methanol/ethyl acetate = 6/6/3 times volume

REFERENCE EXAMPLES

The following compounds were synthesized via the synthetic route shown below.

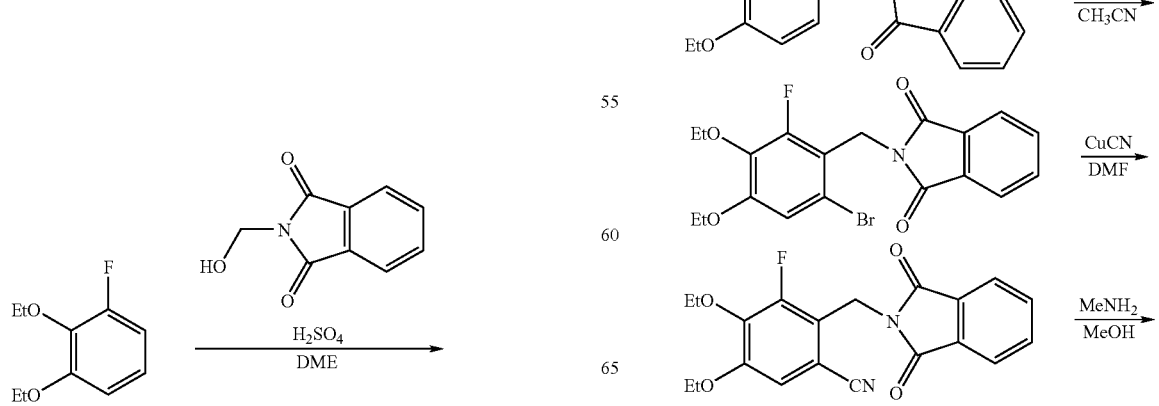

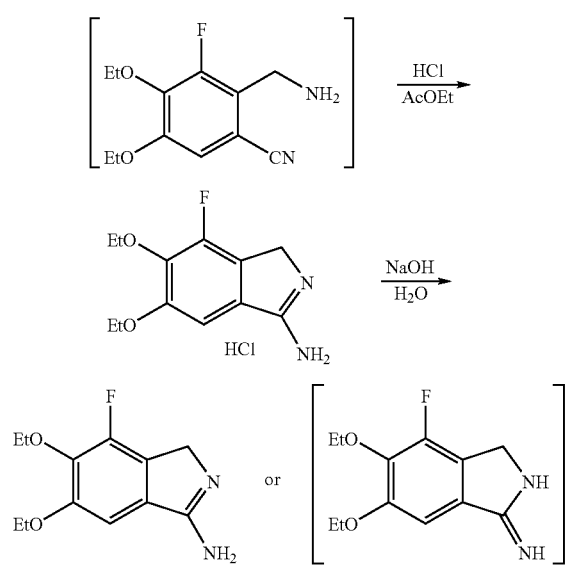

Reference Example 1

Production of 2-(3,4-diethoxy-2-fluorobenzyl)isoindol-1,3-dione

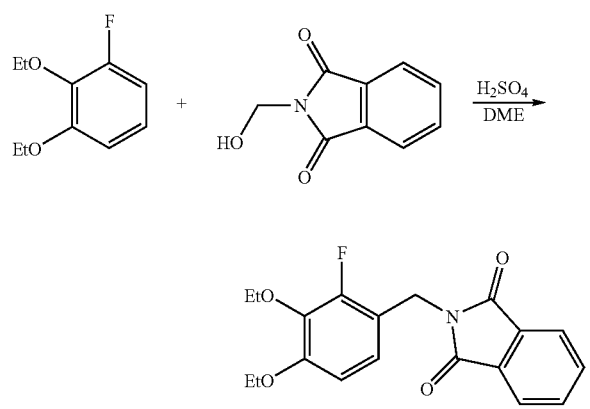

To a solution of 1,2-diethoxy-3-fluorobenzene (2.28 g, 12.4 mol) and N-(hydroxymethyl)phthalimide (2.41 g, 13.6 mol) in 1,2-dimethoxyethane (8 mL), a solution of sulfuric acid (8 mL) in 1,2-dimethoxyethane (8 mL) was added dropwise on ice, and the mixture was stirred at room temperature for twelve hours. The reaction mixture was poured into water (100 mL), and crystals were filtered. The obtained crystals were recrystallized from acetone and water, and the precipitated crystals were filtered. After the filtrate was concentrated under reduced pressure, the residue was crystallized from acetone to give 0.96 g of the title compound (yield: 23%) as white crystals.

$^1$H-NMR (400 MHz, CDCl$_3$) δ: 1.35 (3H, t, J=7.1 Hz), 1.41 (3H, t, J=7.1 Hz), 4.03 (2H, q, J=7.1 Hz), 4.10 (2H, q, J=7.1 Hz), 4.86 (2H, so), 6.60 (1H, dd, J=1.7, 8.5 Hz), 7.00 (1H, t, J=8.1 Hz), 7.71 (2H, dd, J=2.9, 5.4 Hz), 7.85 (2H, dd, J=2.9, 5.4 Hz).

Reference Example 2

Production of 2-(6-bromo-3,4-diethoxy-2-fluorobenzyl)isoindol-1,3-dione

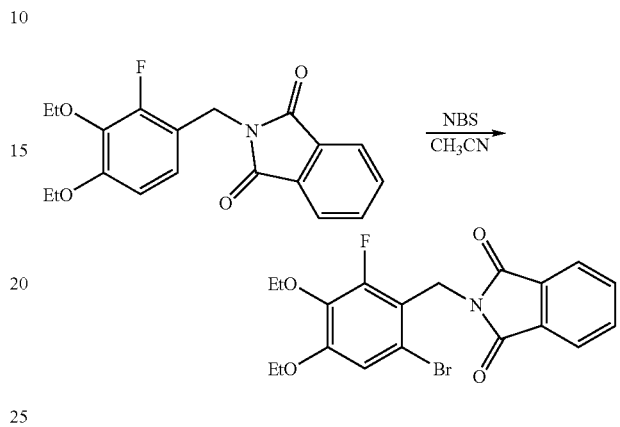

N-bromosuccinimide (1.43 g, 8.07 mol) was added to a solution of 2-(3,4-diethoxy-2-fluorobenzyl)isoindol-1,3-dione (2.52 g, 7.34 mol) in acetonitrile (30 mL) on ice. The mixture was stirred on ice for ten hours, and then at room temperature for six hours. The reaction mixture was extracted after the addition of a 5% aqueous solution of sodium thiosulfate and ethyl acetate; then the resultant organic layer was washed sequentially with 1N hydrochloric acid and a saturated aqueous solution of sodium hydrogen carbonate, and dried over anhydrous magnesium sulfate. After filtration, the solvent was distilled off and the residue was purified by silica gel column chromatography (diethyl ether, no-hexane) to give 1.12 g of the title compound (yield: 36%) as white crystals.

$^1$H-NMR (400 MHz, CDCl$_3$) δ: 1.34 (3H, t, J=7.1 Hz), 1.47 (3H, t, J=7.1 Hz), 4.03 (2H, q, J=7.1 Hz), 4.09 (2H, q, J=7.1 Hz), 4.95 (2H, so), 6.89 (1H, d, J=2.0 Hz), 7.69 (2H, dd, J=3.2, 5.4 Hz), 7.85 (2H, dd, J=2.9, 5.4 Hz).

Reference Example 3

Production of 2-(6-cyano-3,4-diethoxy-2-fluorobenzyl)isoindol-1,3-dione

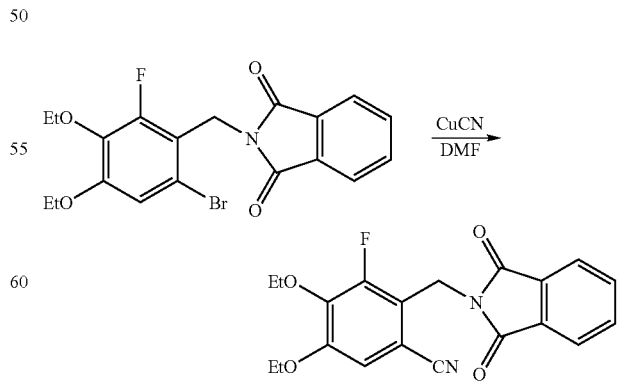

A mixture of 2-(6-bromo-3,4-diethoxy-2-fluorobenzyl)isoindol-1,3-dione (1.00 g, 2.37 mol), copper cyanide (0.42 g, 4.74 mol) and N,N-dimethylformamide (5 mL) was stirred at 155° C. for ten hours. After the reaction mixture was extracted with a 10% aqueous solution of ethylene diamine and toluene, the resultant organic layer was washed sequentially with a 10% aqueous solution of ethylene diamine and saturated brine and dried over anhydrous sodium sulfate. After filtration, the solvent was distilled off to give crude crystals, which were washed with ethyl acetate to give 0.52 g of the title compound (yield: 60%) as slightly green crystals.

$^1$H-NMR (400 MHz, CDCl$_3$) δ: 1.34 (3H, t, J=7.1 Hz), 1.47 (3H, t, J=7.1 Hz), 4.07 (2H, q, J=7.1 Hz), 4.18 (2H, q, J=7.1 Hz), 5.02 (2H, d, J=1.2 Hz), 6.96 (1H, d, J=1.7 Hz), 7.72 (2H, dd, J=2.9, 5.4 Hz), 7.85 (2H, dd, J=2.9, 5.4 Hz).

Reference Example 4

Production of 5,6-diethoxy-4-fluoro-3H-isoindol-1-ylamine hydrochloride

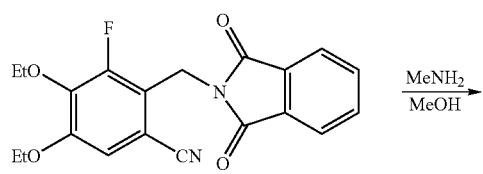

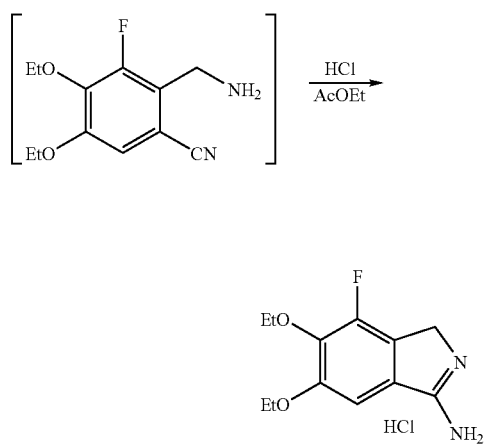

A mixture of 2-(6-cyano-3,4-diethoxy-2-fluorobenzyl)isoindol-1,3-dione (668 mg, 1.81 mol) and 40% methylamine-methanol solution (7 mL) was stirred at 60° C. for two hours. After the solvent of the reaction mixture was distilled off, ethanol (10 mL) and 4N hydrogen chloride-ethyl acetate solution (1 mL) were added to the obtained residue. After the solvent of the reaction mixture was distilled off, the residue was washed with ethyl acetate to give crude crystals which were recrystallized from methanol and ethyl acetate, and 186 mg of the title compound (yield: 58%) was obtained as slightly green crystals.

$^1$H-NMR (400 MHz, DMSO-d$_6$) δ: 1.29 (3H, t, J=7.1 Hz), 1.40 (3H, t, J=7.1 Hz), 4.12 (2H, q, J=7.1 Hz), 4.18 (2H, q, J=7.1 Hz), 4.81 (2H, so), 7.93 (1H, so), 9.27 (1H, bus), 9.72 (1H, bus), 10.42 (1H, bus).

Reference Example 5

Production of 5,6-diethoxy-4-fluoro-3H-isoindol-1-ylamine

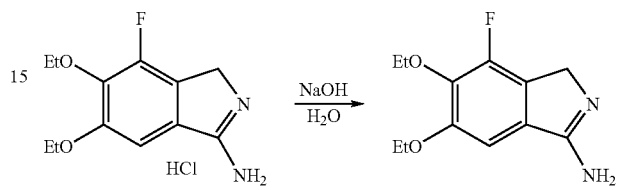

To a mixture of 5,6-diethoxy-4-fluoro-3H-isoindol-1-ylamine hydrochloride (233 mg, 0.85 mol) and water (6 mL), a 1N aqueous solution of sodium hydroxide (2 mL) was added, and the mixture was stirred on ice for 20 minutes. Precipitated crystals were filtered and washed with water to give 85 mg of the title compound (yield: 42%) as slightly green crystals.

$^1$H-NMR (400 MHz, DMSO-d$_6$) δ: 1.25 (3H, t, J=7.1 Hz), 1.37 (3H, t, J=7.1 Hz), 4.04 (2H, q, J=7.1 Hz), 4.08 (2H, q, J=7.1 Hz), 4.41 (2H, so), 6.41 (2H, bus), 7.35 (1H, so).

INDUSTRIAL APPLICABILITY

According to the present invention, the cyano group in the 1st position (meta position to fluorine) of 4,5-dialkyloxy-3-fluorophthalonitrile (compounds (III)) can be reduced with significantly high regioselectivity, by hydrogenating, in a solvent, compounds (III) in the presence of a palladium catalyst and an acid, and 5,6-dialkyloxy-7-fluoro-3H-isoindol-1-ylamine (compounds (II)) can be obtained in high yield through a cyclization reaction of the resultant 6-aminomethyl-3,4-diethoxy-2-fluorobenzonitrile (compounds (I)).

Also, according to the present invention, purification and isolation of the compounds of interest can be performed readily, since the palladium catalyst used is inexpensive and safe with low fire risk, and compound purification can be carried out simply by filtration, extraction, and crystallization, without the need for complicated procedures such as chromatography. Therefore, the methods of the present invention are significantly advantageous for producing isoindole derivatives at an industrial scale compared to conventional technologies.

The invention claimed is:

1. A method for producing an isoindole (compound (II)) with the following formula (II):

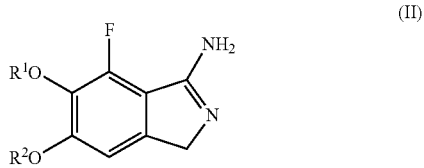

(wherein $R^1$ and $R^2$ each independently represent a $C_{1-6}$ alkyl group) or a salt thereof, comprising the step of cyclizing, in a solvent, compound (I) with the following formula (I):

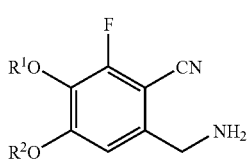

(I)

(wherein $R^1$ and $R^2$ have the same meanings as $R^1$ and $R^2$ in formula (II) above) or a salt thereof, or their hydrate or solvate in the presence of a base (Step 1).

2. The method of claim 1, wherein a compound of formula (I) is prepared by hydrogenation of a compound of formula (III):

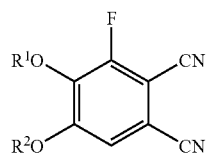

(III)

(wherein $R^1$ and $R^2$ have the same meanings as $R^1$ and $R^2$ in formula (I) above in claim 1) in a solvent in the presence of a palladium catalyst and an acid to obtain compound (I) having the following formula (I):

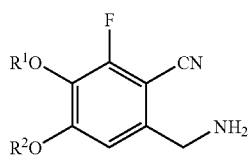

(I)

(wherein $R^1$ and $R^2$ have the same meanings as $R^1$ and $R^2$ in formula (I) above) (Step 2).

3. The method of claim 2, wherein the palladium catalyst is palladium hydroxide, a palladium-carbon catalyst, or Lindlar catalyst.

4. The method of claim 2 or 3, wherein the acid is methanesulfonic acid or sulfuric acid.

5. The method of claim 1, wherein $R^1$ and $R^2$ in formulae (I) to (II) are both ethyl groups.

6. The method of claim 2 wherein $R^1$ and $R^2$ in formula (III) are both ethyl groups.

\* \* \* \* \*